US012582148B2

(12) United States Patent
Lefkowitz et al.

(10) Patent No.: US 12,582,148 B2
(45) Date of Patent: Mar. 24, 2026

(54) COMPOSITIONS AND METHODS FOR IMPROVING QUALITY OF LIFE IN PATIENTS WITH AUTISM SPECTRUM DISORDER

(71) Applicant: FLAASK, LLC, University Heights, OH (US)

(72) Inventors: Andrew R. Lefkowitz, Solon, OH (US); Ken Alibek, Solon, OH (US)

(73) Assignee: FLAASK, LLC, University Heights, OH (US)

( * ) Notice: Subject to any disclaimer, the term of this patent is extended or adjusted under 35 U.S.C. 154(b) by 872 days.

(21) Appl. No.: 17/299,367

(22) PCT Filed: Jan. 25, 2020

(86) PCT No.: PCT/US2020/015124

§ 371 (c)(1),
(2) Date: Jun. 3, 2021

(87) PCT Pub. No.: WO2020/154712

PCT Pub. Date: Jul. 30, 2020

(65) Prior Publication Data

US 2022/0015406 A1 Jan. 20, 2022

Related U.S. Application Data

(60) Provisional application No. 62/796,781, filed on Jan. 25, 2019.

(51) Int. Cl.

| | |
|---|---|
| ***A23L 33/16*** | (2016.01) |
| ***A23L 33/125*** | (2016.01) |
| ***A23L 33/135*** | (2016.01) |
| ***A61K 31/05*** | (2006.01) |
| ***A61K 31/23*** | (2006.01) |
| ***A61K 31/704*** | (2006.01) |
| ***A61K 31/7048*** | (2006.01) |
| ***A61K 33/04*** | (2006.01) |
| ***A61K 35/74*** | (2015.01) |

(52) U.S. Cl.

CPC ............. *A23L 33/16* (2016.08); *A23L 33/125* (2016.08); *A23L 33/135* (2016.08); *A61K 31/05* (2013.01); *A61K 31/23* (2013.01); *A61K 31/704* (2013.01); *A61K 31/7048* (2013.01); *A61K 33/04* (2013.01); *A61K 35/74* (2013.01)

(58) Field of Classification Search

CPC ...... A23L 33/16; A23L 33/125; A23L 33/135; A61K 31/105; A61K 31/23; A61K 31/704; A61K 31/7048; A61K 33/04; A61K 35/74

USPC ........................................................... 514/27

See application file for complete search history.

(56) References Cited

U.S. PATENT DOCUMENTS

| | | | | |
|---|---|---|---|---|
| 6,099,844 | A * | 8/2000 | Rohde, Jr. | C12Y 302/01032 424/754 |
| 9,216,203 | B1 | 12/2015 | Gennaro | |
| 2011/0091431 | A1 | 4/2011 | Olmstead | |
| 2012/0190632 | A1 | 7/2012 | Chen et al. | |
| 2012/0251512 | A1* | 10/2012 | Farmer | A23K 20/20 424/93.46 |
| 2013/0281532 | A1* | 10/2013 | Schlievert | A61K 45/06 514/552 |

FOREIGN PATENT DOCUMENTS

| | | | | |
|---|---|---|---|---|
| CN | 106389479 | * | 2/2017 | A61K 35/745 |
| CN | 106389479 A | | 2/2017 | |
| WO | WO 2014/025905 A1 | * | 2/2014 | A61P 43/00 |
| WO | WO 2016/169573 A1 | * | 10/2016 | A61K 31/343 |
| WO | WO 2017/029683 A1 | * | 2/2017 | A61K 9/0053 |

OTHER PUBLICATIONS

Kurokowa et al, The Journal of Pharmacology and Experimental Therapeutics, 1998, 284(2), 728-735.*
Hegde, Journal: Indian Academy of Clinical Medicine, 2006, 7(1): 16-9, pp. 1-4.*
Mehdi et al, Molecules, 2013, 18, 3292-3311.*
Woodbury et al, Frontiers in Neurology, 2013, 4, 1-6.*
Mnif et al, Peptide Science, online Mar. 23, 2015, 139-147.*
Bhattacharya et al, Sch. Acad. J. Pharm. 2017, 6(7), 320-329.*
Ustundag et al, Critical Reviews in Food Science, 2007, 47, 231-258.*
Eissa et al, Frontiers in Neuroscience, 2018, 12 article 304, pp. 1-26.*
Igwe et al, International Journal of Medical and Pharmaceutical Case Reports, 2015, 495, 125-129.*
Jensen et al, BMC Immunology, 2010, 11(15), 1-14.*
Sil et al, International Journal of Science and Research, 2017, 6(10), 41-50.*
Henderson et al, Autism, 2013, 3(3), 1-4.*

(Continued)

*Primary Examiner* — Ganapathy Krishnan
(74) *Attorney, Agent, or Firm* — SALIWANCHIK, LLOYD & EISENSCHENK

(57) ABSTRACT

The present invention provides compositions and methods for treating a subject diagnosed with ASD. In preferred embodiments, the subject compositions comprise tellimagrandin II, glycyrrhizin, monolaurin, selenium, honokiol, a probiotic, and one or more biological amphiphilic molecules, which when administered to a subject, can support immune and/or digestive health, and suppress and/or disable viral pathogenic agents in the body.

3 Claims, No Drawings

(56) References Cited

OTHER PUBLICATIONS

Jepson, The Physiological Basis and Biomedical Intervention Options of Autism Spectrum Disorder; Children's Biomedical Center of Utah, 2004, pp. 1-57.*
Kim, K., et al., "Characteristics of Sophorolipid as an Antimicrobial Agent." Journal of Microbiology and Biotechnology, 2002, 12(2): 235-241.
Kumar, P., et al., "Correaltion between Viral Infections and Autism: An Overview." Delhi Psychiatry Journal, Oct. 2014, 17(2): 401-412.
Myers, S.M., et al., "Management of Children With Autism Spectrum Disorders." Pediatrics, Nov. 2007, 120(5): 1162-1182.
Sharma, A., et al., "A New Triterpenoid Saponin and Antimicrobial Activity of Ethanolic Extract from Sapindus mukorossi Gaertn." Hindawi Publishing Corporation Journal of Chemistry, 2013, Article ID 218510: pp. 1-5.

* cited by examiner

COMPOSITIONS AND METHODS FOR IMPROVING QUALITY OF LIFE IN PATIENTS WITH AUTISM SPECTRUM DISORDER

CROSS-REFERENCE TO RELATED APPLICATIONS

This application is a National Stage Application of International Application No. PCT/US2020/015124, filed Jan. 25, 2020; which claims priority to U.S. Provisional Patent Application No. 62/796,781, filed Jan. 25, 2019, both of which are incorporated herein by reference in their entirety.

BACKGROUND OF INVENTION

Autism spectrum disorder (ASD) refers to a group of neurodevelopment disorders, including autistic disorder (autism), Asperger syndrome, childhood disintegrative disorder, and pervasive developmental disorders, which are characterized by repetitive, distinctive patterns of behavior and difficulties with social communication and interaction. Subjects with ASD may have a combination of many symptoms and syndromes, which are typically present from early childhood and affect daily functioning.

Included within ASD is a wide range of symptoms, skills, and levels of functional disability. Some children and adults with ASD are fully capable of performing all activities of daily life, while others require substantial support to perform basic life functions and activities. Additionally, individuals with ASD may experience pathologic changes such as brain inflammation, gastrointestinal problems, immune system imbalance, lipid metabolism imbalance, and possible increased risk of cancer due to links between autism and mutations in cancer-associated genes and pathways.

The prevalence of ASD in children in the United States has been increasing rapidly over the past 50 years. At present, the rate of ASD prevalence is 1 case for every 59 children born. Compared to 2016, when it was 1 in 68 children; 2008, when it was 1 in 125 children; and 50 years ago, when it was 1 in 2500 children, the present statistics indicate that ASD prevalence is not only increasing, but actually doubling every ten years.

Considerably more males are affected with ASD than females. For some individuals, the core symptoms of ASD (i.e., impairments in communication and social interaction, and restricted/repetitive behaviors and interests) may improve with intervention and maturation; however, core deficits typically translate into varying developmental presentations that endure throughout the lifespan.

The exact cause of ASD development is not entirely clear, and the underlying root of ASD symptoms, such as damaged brain structures and impaired nerve connections, cannot be readily corrected by existing medications; however, drugs useful in treating other diseases with similar symptoms can be useful in managing ASD, though none have been approved by the FDA for treating ASD specifically.

It is known that ASD does have a genetic component, with heritability estimated to be as high as 90% in some studies. Identification of specific genetic risk variants has proved to be challenging, however, and many researchers suggest that there may be multiple pathways to the disorder, with prenatal and postnatal insult potentially contributing to its development in some instances. For example, certain metabolic and other maternal conditions (e.g., diabetes, hypertension, obesity and infection), as well as consumption of alcohol and certain medications (e.g., antidepressants) during pregnancy may be associated with increased risk of ASD in offspring.

Additionally, maternal immune malfunction during pregnancy, including chronic immune activation of microglia, may also cause some alterations in a child's brain. The connection is explained by possible upregulation of brain inflammatory cytokines resulting from immune activation in the mother, which then leads to presence of these cytokines in sera and frontal and cingulate cortices of the fetal brain. This is thought to affect the course of brain development, which may lead to ASD.

Much of the research into ASD etiology points to congenital chronic infections as a cause for development of the disorder. Many of these infections are viral, including Herpes Simplex Virus (HSV) 1 and 2, Human Herpes Virus (HHV) 6, Epstein-Barr Virus, Rubella virus, Measles virus, Cytomegalovirus (CMV), BK virus, JK virus, SV40 virus, and others.

For example, it was reported in 2005 that in the USA, approximately 40,000 children are born with congenital cytomegalovirus (CMV) infection, and Binda et al. found that congenital CMV was found 10 times more often in blood of children with ASD than in healthy children. Human herpes virus-6 was found in children with ASD 3.5 times more often than within healthy children. Epstein-Barr virus (EBV) was found in patients with multiple sclerosis and ASD. Congenital rubella syndrome caused by transmission of rubella virus from mother to fetus also strongly affects the brain development, and children with ASD are infected 200 times more often than healthy children. Additionally, the combination of three viruses: BK virus, JC virus and simian virus 40 was found two times more often in children with ASD than in healthy controls.

Furthermore, the roles of herpes simplex viruses (HSV) 1 and 2 in influencing the development of a number of neurodevelopmental disorders, including schizophrenia, Alzheimer's disease, epilepsy, and ASD have also been studied.

The mechanism by which viral infection may lead to autism is not yet clear. One theory is that, once a subject is infected, many viruses have the ability to localize in certain brain sections, or through infection elsewhere in the body, trigger disease in the central nervous system. This might in turn disturb normal brain development. The mechanism may also occur through immune responses in the mother while a fetus is developing, which may lead to weakening of the fetus's immune system and further lead to disturbances in brain development.

There is no cure for ASD, but current therapies and behavioral interventions exist, which are designed to improve certain symptoms of the disorder; however, most existing treatments focus on treating the brain and cognitive functions specifically, rather than the other potential underlying causes of ASD and its symptoms, for example, compromised immune health.

The ideal treatment plan for a subject diagnosed with ASD coordinates therapies and interventions that meet the specific needs of the individual, based on where he or she falls on the spectrum. Most health care professionals agree that the earlier the intervention, the better.

Thus, there is a continuing need for new, integrated compositions and methods for treating a broad range of ASD symptoms and improving the overall quality of life and performance for patients—particularly children—diagnosed with autism and its spectra.

BRIEF SUMMARY

The present invention provides compositions and methods for improving cognitive, immune and/or digestive functioning in subjects with autism spectrum disorder (ASD) and other conditions. Advantageously, embodiments of the present invention provide compositions and methods for modulating the immune system and improving the quality of life for subjects, particularly children, with ASD.

In certain embodiments, the present invention provides a supplement composition for improving the quality of life for a subject diagnosed with ASD, wherein the composition helps support immune health and suppress infectious agents in the subject's body.

In one embodiment, the supplement composition comprises tellimagrandin II, glycyrrhizin, monolaurin, selenium, omega-3 fatty acids, honokiol, and a probiotic (e.g., *Bacillus coagulans* BC-30).

In one embodiment the supplement composition comprises, consists of, or consists essentially of tellimagrandin II, glycyrrhizin, monolaurin, selenium, omega-3 fatty acids, honokiol, and a probiotic (e.g., *Bacillus coagulans* BC-30).

In certain embodiments, the supplement composition further comprises a biological amphiphilic molecule. In a specific embodiment, the biological amphiphilic molecule is a surfactant, preferably a biosurfactant. Biosurfactants are surface active compounds that lower the surface and interfacial tension between individual molecules at respective surfaces and interfaces. Among other capabilities, biosurfactants provide additional immune support against viral infections, and enhance the bioavailability of the other components of the supplement composition.

In one embodiment, the biosurfactant is a glycolipid produced by, for example, a yeast. In a specific embodiment, the glycolipid is a sophorolipid (SLP). In one embodiment, the biosurfactant is a lipopeptide produced by a bacteria. In a specific embodiment, the lipopeptide is surfactin.

In one embodiment, the biological amphiphilic molecule is a saponin. Saponins are surfactants that are found in many plants and that exhibit similar characteristics to microbial biosurfactants.

In one embodiment, the components of the supplement composition are formulated as a mixture, comprising optional additional ingredients, such as, for example, a pharmaceutically-acceptable carrier.

In one embodiment, the supplement composition is formulated into a biosurfactant delivery system, wherein a biosurfactant forms a liposome, or a micro- or nano-capsule, with the other components of the supplement composition encapsulated therein. In one embodiment, additional biological polymers can be included to provide further structure for encapsulation.

Biosurfactant encapsulation can enhance the bioavailability of the supplement composition by protecting its components from elements in the blood, such as proteins and other molecules, that otherwise might bind to a compound or composition and prevent it from reaching a target site. Additionally, the encapsulated delivery system can allow for compounds that might otherwise be degraded by acids or enzymes in the GI tract to be administered orally, as it creates a barrier against the acids or enzymes. Furthermore, the biosurfactant-encapsulated delivery system formulation allows for time release of the compound(s) therein, thereby reducing the potential toxicity or potential negative side-effects in a subject.

In certain embodiments, the present invention provides a method for improving the quality of life for a subject diagnosed with ASD and/or a condition wherein the immune system is activated and/or malfunctioning, said method comprising administering to the subject a therapeutically-effective amount of a supplement composition of the present invention.

In one embodiment, the method can be used to treat symptoms of ASD, including behavioral, mental, emotional and/or physiological symptoms.

In one embodiment, the method first comprises testing the subject for, and/or diagnosing the subject with, ASD and/or another condition, such as a viral infection. In one embodiment, the method can first comprise testing the subject for signs of poor immune health, for example, by testing the subject for immune markers such as T-cells and NK cells. In one embodiment, the testing is performed using known blood testing methods, including blood antibody tests, and in the case of viruses that cause, for example, external lesions, sampling, culturing and polynucleotide sequencing.

In one embodiment, the subject being treated according to the present invention has previously contracted an infection, currently has an infection, or has been exposed to one or more infectious agents. In preferred embodiments, the infection is due to a chronic virus.

In one embodiment, the subject is diagnosed specifically with autistic disorder or autism. In on embodiment, the subject is diagnosed with one or more of cytomegalovirus (CMV), Epstein-Barr virus (EBV), rubella virus, measles virus, herpes simplex virus (HSV) type 1 or 2, herpes zoster, varicella-zoster virus (VZV), HHV6, HHV7, other herpes family viruses, or any other chronic, congenital, persistent, latent, dormant, acute and/or subacute viral infection.

The subject of the present invention can be any human diagnosed with ASD. In one embodiment, the human subject is a child or adolescent, for example, 16 years of age or younger.

Advantageously, the present invention can improve the quality of life for subjects who are diagnosed with, for example, ASD and/or a viral infection. Improved quality of life can include, for example, improvement of mental, emotional and/or physiological symptoms of ASD, improvement in behavioral performance, and improvement in signs and symptoms of viral infections.

DETAILED DISCLOSURE

The present invention provides compositions and methods for improving cognitive, immune and/or digestive functioning in subjects with autism spectrum disorder (ASD) and other conditions. Advantageously, embodiments of the present invention provide compositions and methods for modulating the immune system and improving the quality of life for subjects, particularly children, with ASD.

Selected Definitions

As used herein, the term "subject" can include any human diagnosed with ASD. The preferred subject in the context of this invention is a human of any gender and at any age or stage of development, including infant, toddler, adolescent, teenager, adult, middle-aged and senior. In one embodiment, the human subject is a child or adolescent, for example, 16 years of age or younger.

The terms "autism spectrum disorder" and "ASD" are used in this disclosure to refer to a spectrum of disorders characterized by abnormalities of social interactions and communication, as well as restricted interests and repetitive behavior. This spectrum includes, but is not limited to, autistic disorder (autism), Asperger's syndrome, childhood disintegrative disorder, atypical autism or pervasive developmental disorder not otherwise specified (PPD-NOS), as well as Rett syndrome and tuberous sclerosis.

As used herein, "treating" or "treatment" means the eradicating, improving, reducing, ameliorating or reversing of at least one sign or symptom of a condition or disorder. Treatment can include, but does not require, a complete cure of the condition or disorder, meaning treatment can also include partial eradication, improvement, reduction, amelioration or reversal. Treatment can also include delaying, forestalling and/or inhibiting the progression of a condition or disorder to a more severe condition or disorder.

The terms "therapeutically effective" amount or dose, "effective amount," and "effective dose" are used in this disclosure to refer to an amount of a compound or composition that, when administered to a subject, is capable of providing a desired therapeutic effect or a desired level or treatment. The actual amount of the compound or composition will vary depending on a number of factors including, but not limited to, the particular disorder being treated, the severity of the disorder, the size and health of the patient, and the route of administration. A skilled medical practitioner can readily determine the appropriate amount using methods known in the medical arts.

A plant "extract," as used herein, refers to the material resulting from exposing a plant part to a solvent and removing the solvent, or from using various chemical, immunological, biochemical or physical procedures known to those of skill in the art, including but not limited to, precipitation, centrifugation, filtering, column chromatography, and detergent lysis. Plant material can include, for example, roots, stems, leaves, flowers, seeds, fruits, pollen, or parts thereof.

As used herein, the term "probiotic" refers to microorganisms, which, when administered in adequate amounts, confer a health benefit on the host. In preferred embodiments, the microorganisms are live and/or in spore form.

The terms "isolated" or "purified," when used in connection with biological or natural materials such as nucleic acid molecules, polynucleotides, polypeptides, proteins, organic compounds, such as small molecules, microorganism cells/strains, or host cells, means the material is substantially free of other compounds, such as cellular material, with which it is associated in nature. That is, the materials do not occur naturally without these other compounds and/or have different or distinctive characteristics compared with those found in the native material.

In certain embodiments, purified compounds are at least 60% by weight the compound of interest. Preferably, the preparation is at least 75%, more preferably at least 90%, and most preferably at least 99% or 100% (w/w) of the desired compound by weight. Purity is measured by any appropriate standard method, for example, by column chromatography, thin layer chromatography, or high-performance liquid chromatography (HPLC) analysis.

The description herein of any aspect or embodiment of the invention using terms such as "comprising," "having," "including," or "containing" with reference to an element or elements is intended to provide support for a similar aspect or embodiment of the invention that "consists of," "consists essentially of," or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

The term "consisting essentially of," as used herein, limits the scope of the ingredients and steps to the specified materials or steps and those that do not materially affect the basic and novel characteristic(s) of the present invention.

Supplement Compositions

In certain embodiments, the present invention provides a supplement composition for improving the quality of life for a subject diagnosed with ASD, wherein the composition helps support immune health and suppress infectious agents in the subject's body.

In one embodiment, the combination of ingredients in the composition creates a synergistic effect towards immune support and/or suppression of infectious agents.

In one embodiment, the supplement composition comprises tellimagrandin II, glycyrrhizin, monolaurin, selenium, omega-3 fatty acids, honokiol, and a probiotic (e.g., *Bacillus coagulans* BC-30).

In one embodiment the supplement composition comprises, consists of, or consists essentially of tellimagrandin II, glycyrrhizin, monolaurin, selenium, omega-3 fatty acids, honokiol, and a probiotic (e.g., *Bacillus coagulans* BC-30).

In certain embodiments, the supplement composition further comprises a biological amphiphilic molecule. In a specific embodiment, the biological amphiphilic molecule is a surfactant, preferably a biosurfactant. In one embodiment, the biological amphiphilic molecule is a saponin.

In one embodiment, the composition comprises tellimagrandin II. Tellimagrandin II is an active compound derived from *Syzygium aromaticum*, the tree with flower buds commonly known as cloves. Additionally, tellimagrandin II can also be extracted from *Geum japonicum* and some other plants.

This substance is active against HSV and CMV, which have developed acyclovir and phosphonoacetic acid (PAA) resistant strains. In some embodiments, tellimagrandin II contributes to the effectiveness of the supplement composition by reducing viral yields through, for example, inhibition of viral DNA synthesis.

In certain embodiments, the amount of tellimagrandin II in one dosage of the supplement composition is about 20 mg to about 5,000 mg, preferably about 100 mg to about 4500 mg, more preferably about 150 mg to about 3,500 mg.

In one embodiment, the composition comprises glycyrrhizin. Glycyrrhizin is an active compound derived from *Glycyrrhiza uralensis* and *Glycyrrhiza glabra*, otherwise known as licorice root. Structurally, glycyrrhizin is a saponin that can be used as an emulsifier in food and cosmetic products.

This substance exhibits activity against viruses including VZV, SARS coronavirus, EBV, HIV-1, hepatitis, and influenza A virus. In some embodiments, glycyrrhizin contributes to the effectiveness of the supplement composition by reducing viral yields and/or inhibiting plaque formation through, for example, interfering with the virus's replication cycle at the attachment, penetration, uncoating and/or particle release stages. Furthermore, glycyrrhizin can have additional therapeutic effects on, for example, the liver where a viral infection has caused liver dysfunction.

In certain embodiments, the amount of glycyrrhizin in one dosage of the supplement composition is about 5 mg to about 200 mg, preferably about 50 mg to about 100 mg.

In one embodiment, the composition comprises monolaurin, which is the glycerol ester of lauric acid. Lauric acid is an active antiviral and antibacterial substance found in human breast milk, and comprises about 50% of the saturated fat content of coconut oil. When ingested, lauric acid is converted to monolaurin, which is more biologically active than lauric acid.

Monolaurin is active against influenza virus, pneumovirus, Paramyxovirus (Newcastle), Coronavirus (Avian Infectious, Bronchitis virus), herpes simplex I & II, CMV, EBV, HIV, measles, leukemia virus, Simliki forest virus, HPV, Visna virus, Vesicular stomatitits virus, respiratory syncytial virus, Dengue virus (type 1-4), and lymphocytic choriomeningitis.

In some embodiments, monolaurin contributes to the effectiveness of the supplement composition by reducing viral yields through, for example, prevention of viral attachment to susceptible host cells, prevention of viral replication, disruption of the virus lipid bylayer, and disintegration of the viral envelope.

Monolaurin provides additional benefits to a subject due to its effectiveness against Gram-positive bacteria, including, e.g., Anthrax, *Listeria monocytogenes, Staphylococcus aureus*, Groups A, B, F, and G streptococci, *Streptococcus agalactiae*, Mycobacteria *Clostridium perfringens* and Gram-negative bacteria, including, e.g., *Chlamydia pneumonia, Neisseria gonorrhoeae, Helicobater pylori, Mycoplasma pneumonia*, and *Vibrio parahaemolyticus*; against yeast, fungi and molds, including, e.g., *Aspergillus niger, Saccharomyces cerevisiae*, Ringworm/Tinea, *Malassezia* species, *Penicillium citrinum*, and *Candida utilis*; and against a number of protozoa, including, e.g., *Giardia lamblia.*

In certain embodiments, the amount of monolaurin in one dosage of the supplement composition is about 500 mg to about 4,000 mg, preferably about 600 mg to about 3,500 mg, more preferably about 750 mg to about 3,000 mg.

In one embodiment, the composition comprises selenium. Selenium is a trace mineral that can be found in soils, plants and animal tissue. For example, nuts, fresh and saltwater fish, grains, beef and poultry are all sources of selenium when ingested. The selenium can be in an inorganic form (e.g., selenate or selenite), and/or an organic form (e.g., selenomethionine and selenocysteine).

Selenium is an essential mineral for animals, including humans. It is incorporated into selenoproteins, which have a wide range of pleiotropic effects, ranging from antioxidant and anti-inflammatory effects to the production of active thyroid hormone. Selenium is also indicated as providing support for cognitive health, reproductive health, and immune health. Accordingly, selenium deficiency has been associated with increased risk of mortality, poor immune function, and cognitive decline.

Selenium deficiency has also been associated with increased viral pathogenesis, in part due to immune dysfunction. Thus, in some embodiments, selenium contributes to the effectiveness of the supplement composition by supporting a subject's immune system in fighting viral invaders.

In certain embodiments, the amount of selenium in one dosage of the supplement composition is about 10 to about 150 μg, preferably about 20 to about 70 μg, more preferably about 30 to about 60 μg.

In one embodiment, the supplement composition comprises honokiol. Honokiol is a poly-phenolic compound that can be extracted from the bark of *magnolia* species, e.g., *Magnolia grandiflora* and *Magnolia dealbata*. Honokiol has a strong, spicy fragrance.

The compound has been found to exhibit anxiolytic, analgesic, antidepressant, antithrombotic, antimicrobial, antispasmodic, anti-tumorigenic, and antioxidant properties. Furthermore, honokiol is indicated as a neuronal growth promoter, and a facilitator for $GABA_A$ receptors and for DNA repair. Thus, in some embodiments, honokiol contributes to the effectiveness of the supplement composition through, for example, a variety of neuroprotective mechanisms that result in recovery, regeneration and/or rescue of damaged nervous system structures and functioning.

In certain embodiments, the honokiol is added to the composition in the form of *magnolia* bark extract. The amount honokiol in one dosage of the supplement composition is preferably about 0.5 to 500 μg/kg of body weight, or 0.7 to 70 μg/kg. Preferably the concentration of honokiol is less than 100 μM. In one embodiment, the concentration is about 0.01 to about 10 μM.

In one embodiment, the supplement composition comprises omega-3 fatty acids. Omega-3's are polyunsaturated fatty acids having a double bond three atoms from the terminal methyl group. There are three types of omega-3's involved in human physiology: alpha-linolenic acid (ALA), which is found in many plant oils, eicosapentaenoic acid (EPA) and docosahexaenoic acid (DHA), which are both found in many fish due to their ingestion of EPA- and DHA-rich marine algae and phytoplankton.

Omega-3's promote nervous tissue growth and function, and regulate signal transduction and gene expression. Additionally, they are thought to help reduce oxidative stress on neuronal tissue, as well as promote healing and protect against reduced plasticity after traumatic brain injury. Furthermore, deficiencies in DHA are associated with deficits in neuronal arborization, serotonin, neurocognition, and mesocorticolimbic dopamine neurotransmission, along with elevated anxiety, aggression, and depression.

Thus, in some embodiments, omega-3 contributes to the effectiveness of the supplement composition through promotion of neurocognitive health, for example, by promoting neural growth and healing, and protecting form neuronal death and/or deficits.

In a specific embodiment, the supplement composition comprises DHA. In one embodiment, the supplement composition comprises a combination of omega-3's. In certain embodiments, the amount of total omega-3 fatty acids in one dosage of the supplement composition is about 100 to 1,000 mg, or 200 to 800, or 300 to 500 mg.

In one embodiment, the supplement composition comprises *Bacillus coagulans* GBI-30 (BC30). BC30 is a preferred probiotic for the present invention because it is capable of surviving the acidity of the stomach, thus allowing it to reach the small intestine.

BC30 promotes digestive health in a subject in a variety of ways, which is especially important for children with ASD, a large percentage of whom suffer from some form of digestive ailment. BC30 increases protein and carbohydrate absorption in the small intestine. It can also improve the symptoms of irritable bowel syndrome, such as bloating, pain in the stomach, discomfort, and urgency.

Moreover, BC30 may also out-compete other harmful bacteria that cause infections or may have other deleterious effects. BC30 may delay the onset of symptoms and promote quicker recovery from infection and/or colitis caused by *Clostridium dificile*. BC30 may also be helpful in replenishing beneficial bacteria in the intestines for individuals who have been prescribed antibiotics. Thus, through balance of gut microbiota and inhibition of toxic and/or inflammatory compounds that affect the brain, BC30 can be used for regulating the microbiota-gut-brain axis and its effect on subjects with ASD.

BC30 is further useful for directly and indirectly responding to viral infections. For example, BC30 can inhibit various human herpes viruses, including HHV-1, HHV-2 and HHV-3. Additionally, BC30 can increase the immune response to viral agents through, for example, increased production of T-cells in response to viral infections.

In one embodiment, BC30 contributes to the effectiveness of the supplemental composition through improved digestive and immune health by, for example, reducing inflammation, regulating imbalances in lipid metabolism, and increasing direct and indirect immune response to deleterious bacterial and/or viral agents.

In one embodiment, BC30 is present in the composition in amounts from $1\times10^8$ to $1\times10^{12}$ CFU, preferably $1\times10^9$ to $1\times10^{11}$ CFU, and more preferably 2 billion CFU per dosage. In preferred embodiments, BC30 is in spore form.

In preferred embodiments, the supplement composition further comprises a biological amphiphilic molecule. In certain embodiments, the concentration of biological amphiphilic molecule is about 5% or less, preferably about 0.5% to about 2.5%, more preferably about 0.7 to 1.5%. In one embodiment, more than one biological amphiphilic molecule is used in the supplement composition.

In a specific embodiment, the biological amphiphilic molecule is a surfactant, preferably a biosurfactant. Biosurfactants are surface active compounds that lower the surface and interfacial tension between individual molecules at respective surfaces and interfaces. Among other capabilities, biosurfactants provide additional immune support against viral, bacterial and fungal infections, and enhance the bioavailability of the other components of the supplement composition.

Biosurfactants are biodegradable and can be produced using selected organisms on renewable substrates. Most biosurfactant-producing organisms produce biosurfactants in response to the presence of a hydrocarbon source (e.g., oils, sugar, glycerol, etc.) in the growing media. Microbial biosurfactants are produced by a variety of microorganisms, such as, for example, *Pseudomonas* spp. (*P. aeruginosa, P. putida, P. florescens, P. fragi, P. syringae*); *Flavobacterium* spp.; *Bacillus* spp. (*B. subtilis, B. pumillus, B. licheniformis, B. amyloliquefaciens, B. cereus*); *Wickerhamomyces* spp. (e.g., *W. anomalus*), *Candida* spp. (e.g., *C. albicans, C. rugosa, C. tropicalis, C. lipolytica, C. torulopsis*); *Rhodococcus* spp.; *Arthrobacter* spp.; *Campylobacter* spp.; *Cornybacterium* spp.; *Pichia* spp. (e.g., *P. anomala, P. guilliermondii. P. occidentalis*); *Starmerella* spp. (e.g., *S. bombicola*); and so on.

All biosurfactants are amphiphiles. They consist of two parts: a polar (hydrophilic) moiety and non-polar (hydrophobic) group. The hydrocarbon chain of a fatty acid acts as the common lipophilic moiety of a biosurfactant molecule, whereas the hydrophilic part is formed by ester or alcohol groups of neutral lipids, by the carboxylate group of fatty acids or amino acids (or peptides), by organic acids in the case of flavolipids, or, in the case of glycolipids, by a carbohydrate.

Due to their amphiphilic structure, biosurfactants accumulate at interfaces, thus reducing interfacial tension and leading to the formation of aggregated micellar structures in solution, increase the surface area of hydrophobic water-insoluble substances and increase the water bioavailability of such substances.

The amphiphilic structure of biosurfactants also allows for self-association and interaction with biological membranes. Additionally, the ability of biosurfactants to form pores and destabilize biological membranes permits their use as, e.g., antiviral, antibacterial, antifungal, and hemolytic agents. Combined with the characteristics of low toxicity and biodegradability, biosurfactants are advantageous for use in a variety of application, including human health.

Biosurfactants include glycolipids, lipopeptides, flavolipids, phospholipids, fatty acid esters, and high molecular weight polymers such as lipoproteins, lipopolysaccharide-protein complexes, and polysaccharide-protein-fatty acid complexes.

In one embodiment, the biosurfactants according to the present invention are selected from glycolipids, such as rhamnolipids (RLP), sophorolipids (SLP), trehalose lipids (TL), cellobiose lipids and/or mannosylerythritol lipids (MEL).

In one embodiment, the biosurfactants are selected from lipopeptides, including, for example, surfactin, iturin, fengycin and/or lichenysin.

In one embodiment, the biosurfactants are phospholipids, such as phosphatidylglycerol and/or cardiolipin.

In preferred embodiments, the composition comprises a glycolipid biosurfactant. In a specific embodiment, the glycolipid is a purified SLP._Sophorolipids are glycolipid biosurfactants produced by, for example, various yeasts of the *Starmerella* clade, e.g., *S. bombicola*. SLP consist of a disaccharide sophorose linked to long chain hydroxy fatty acids. They can comprise a partially acetylated 2-O-β-D-glucopyranosyl-D-glucopyranose unit attached β-glycosidically to 17-L-hydroxyoctadecanoic or 17-L-hydroxy-Δ9-octadecenoic acid. The hydroxy fatty acid is generally 16 or 18 carbon atoms, and may contain one or more unsaturated bonds. Furthermore, the sophorose residue can be acetylated on the 6- and/or 6'-position(s). The fatty acid carboxyl group can be free (acidic or linear form (General Formula 1)) or internally esterified at the 4"-position (lactonic form (General Formula 2)). *S. bombicola* produces a specific enzyme, called *S. bombicola* lactone esterase, which catalyzes the esterification of linear SLP to produce lactonic SLP.

In preferred embodiments, the SLP according to the subject invention are represented by General Formula (1) and/or General Formula (2), and include 30 or more types of structural homologues having different fatty acid chain lengths ($R^3$), and, in some instances, having an acetylation or protonation at $R^1$ and/or $R^2$.

(1)

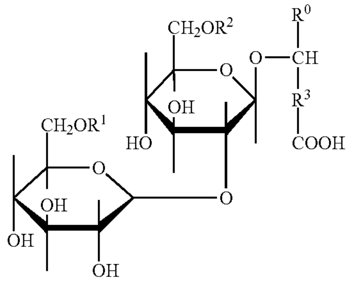

(2)

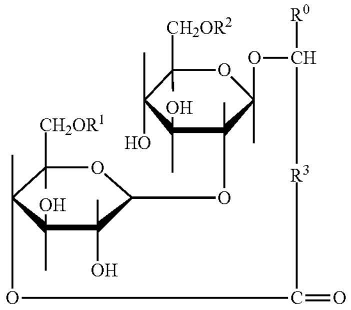

In General Formula (1) or (2), $R^0$ can be either a hydrogen atom or a methyl group. $R^1$ and $R^2$ are each independently a hydrogen atom or an acetyl group. $R^3$ is a saturated aliphatic hydrocarbon chain, or an unsaturated aliphatic hydrocarbon chain having at least one double bond, and may have one or more Substituents.

Examples of the Substituents include halogen atoms, hydroxyl, lower (C1-6) alkyl groups, halo lower (C1-6) alkyl groups, hydroxy lower (C1-6) alkyl groups, halo lower (C1-6) alkoxy groups, and the like. $R^3$ typically has 11 to 20 carbon atoms, preferably 13 to 17 carbon atoms, and more preferably 14 to 16 carbon atoms. Examples of the halogen atoms or halogen atoms bound to alkyl groups or alkoxy groups include fluorine, chlorine, bromine, and iodine.

In one embodiment, the sophorolipid is an acidic SLP. In one embodiment, the sophorolipid is a non-acetylated acidic SLP.

SLP can have antiviral properties against EBV and HSV, as well as against several pathogenic bacteria, such as *Escherichia coli, Moraxella* sp., *Ralstonia eutropha, Rhodococcus erythropolis*, and *Salmonella choleraesuis*. Additionally, SLP can inhibit microbial quorum sensing and destroy biofilms and/or inhibit their formation. This is particularly useful for treating infections, as biofilm formation by viruses and bacteria allows them to develop resistance to drugs and enhances their pathogenicity.

Thus, in some embodiments, SLP contribute to the effectiveness of the supplement composition through, for example, biofilm disruption and direct antiviral activity. SLP provide additional benefits to a subject, including, for example antibacterial and anti-inflammatory properties.

In some embodiments, the composition comprises a lipopeptide biosurfactant. In a specific embodiment, the lipopeptide biosurfactant is surfactin. Lipopeptides are produced by a variety of probiotics and other bacteria, such as, e.g., *Bacillus* natto. *Bacillus coagulans, Bacillus subtilis, Bacillus amyloliquefaciens*, lactic acid bacteria, and others.

Surfactin, in particular, is one of the most powerful lipopeptide biosurfactants. Surfactin is produced by, e.g., *B. subtilis* and *B. amyloliquefaciens*, and has antimicrobial, antitumor, antiviral and antiadhesive properties. It can inhibit fibrin clot formation, induce formation of ion channels in lipid bilayer membranes, and inhibit cyclic adenosine monophosphate (cAMP). The antiviral activity of surfactin is likely due to disruption of the viral lipid membrane.

Thus, in some embodiments, surfactin contributes to the effectiveness of the supplement composition through, for example, direct antiviral activity. Surfactin provides additional benefits to a subject, including, for example, antibacterial and anti-cancer properties.

In one embodiment, the biological amphiphilic molecule is a saponin. Saponins are surfactants that are found in many plants and that exhibit similar characteristics to microbial biosurfactants, for example, self-association and interaction with biological membranes. There are three basic categories of saponins, including triterpenoid saponins, steroidal saponins, and steroidal glycoalkaloids.

Some well-known triterpenoid saponin-accumulating plant families include the Leguminosae, Amaranthaceae, Apiaceae, Caryophyllaceae, Aquifoliaceae, Araliaceae, Cucurbitaceae, Berberidaceae, Chenopodiaceae, Myrsinaceae and Zygophyllaceae, among many others. Legumes such as soybeans, beans and peas are a rich source of triterpenoid saponins. The steroidal saponins are typically found in members of the Agavaceae, Alliaceae, Asparagaceae, Dioscoreaceae, Liliaceae, Amaryllidaceae, Bromeliaceae, Palmae and Scrophulariaceae families and accumulate in abundance in crop plants such as yam, alliums, asparagus, fenugreek, *yucca* and *ginseng*. The steroidal glycoalkaloids are commonly found in members of the Solanaceae family including tomato, potato, aubergines and *capsicum*.

One notable characteristic of many saponins is their ability to inhibit P-glycoproteins. P-glycoprotein (P-gp) is a member of the ATP-dependent membrane transport proteins and is known to pump substrates out of cells in ATP-dependent mechanisms. The over-expression of P-gp in tumor cells reduces intracellular drug concentrations, which decreases the efficacy of a broad spectrum of antitumor drugs. Accordingly, inhibiting P-gp potentially enhances the cellular bioavailability of some of these compounds.

Thus, in some embodiments, saponins contribute to the effectiveness of the supplement composition by, for example, enhancing the bioavailability of the other compounds present in the composition.

Formulation and Delivery of Supplement Compositions

The supplement composition can be formulated to be administered via any route of administration, including, for example, orally, via injection (e.g., intravenous (IV), intramuscular (IM), intraperitoneal, intrathecal or subcutaneous), transdermal, rectal, urogenital (e.g., vaginal), ocular, aural, nasal, inhalation and cutaneous routes.

In one embodiment, the components of the supplement composition are formulated as a mixture, comprising optional additional ingredients, such as, for example, one or more pharmaceutically-acceptable carriers and/or excipients.

The pharmaceutically acceptable carriers and/or excipients, and can be formulated into preparations in, for example, solid, semi-solid, liquid or gaseous forms, such as tablets, capsules, powders, granules, ointments, gels, lotions, solutions, suppositories, drops, patches, injections, inhalants and aerosols.

The term "pharmaceutically acceptable" as used herein means compatible with the other ingredients of a pharmaceutical composition and not deleterious to the recipient thereof.

Carriers and/or excipients according the present invention can include solvents, diluents, buffers (such as, e.g., neutral buffered saline, phosphate buffered saline, or optionally Tris-HCl, acetate or phosphate buffers), oil-in-water or water-in-oil emulsions, aqueous compositions with or without inclusion of organic co-solvents suitable for, e.g., IV use, solubilisers (such as, e.g., Tween 80, Polysorbate 80), colloids, dispersion media, vehicles, fillers, chelating agents (such as, e.g., EDTA or glutathione), amino acids (such as, e.g., glycine), proteins, disintegrants, binders, lubricants, wetting agents, emulsifiers, sweeteners, colorants, flavorings, aromatisers, thickeners, coatings, preservatives (such as, e.g., Thimerosal, benzyl alcohol), antioxidants (such as, e.g., ascorbic acid, sodium metabisulfite), tonicity controlling agents, absorption delaying agents, adjuvants, bulking agents (such as, e.g., lactose, mannitol) and the like.

In some cases, the carriers can be, for example, sterile aqueous or non-aqueous solutions, suspensions, or emulsions. Examples of non-aqueous solvents include, without limitation, propylene glycol, polyethylene glycol, vegetable oils, and organic esters. Aqueous carriers include, without limitation, water, alcohol, saline, and buffered solutions. Acceptable carriers also can include physiologically acceptable aqueous vehicles (e.g., physiological saline) or other known carriers appropriate to specific routes of administration. The use of carriers and/or excipients in the field of drugs and supplements is well known. Except for any conventional media or agent that is incompatible with the supplement composition or with, its use in the present compositions may be contemplated.

In one embodiment, the supplement composition is formulated so that it can be delivered to a subject orally. In particular, the composition is formulated as an orally-consumable product.

Orally-consumable products according to the invention are any preparations or compositions suitable for consumption, for nutrition, for oral hygiene or for pleasure, and are products intended to be introduced into the human or animal oral cavity, to remain there for a certain period of time and then to either be swallowed (e.g., food ready for consumption) or to be removed from the oral cavity again (e.g. chewing gums or products of oral hygiene or medical mouth washes). These products include all substances or products intended to be ingested by humans or animals in a processed, semi-processed or unprocessed state. This also includes substances that are added to orally-consumable products (e.g., active ingredients such as extracts, nutrients, supplements, or pharmaceutical products) during their production, treatment or processing and intended to be introduced into the human or animal oral cavity.

Orally-consumable products can also include substances intended to be swallowed by humans or animals and then digested in an unmodified, prepared or processed state. These include casings, coatings or other encapsulations that are intended also to be swallowed together with the product or for which swallowing is to be anticipated.

The orally-consumable product according to the invention can be a composition to be consumed for nutrition or pleasure. These particularly include baked goods (e.g., bread, dry biscuits, cake, cookies, brownies and other pastries), sweets and candies (e.g., chocolates, chocolate bar products, other bar products, gummies, fruit leathers, jelly beans, coated tablets, hard candies, toffees and caramels, and chewing gum), non-alcoholic beverages (e.g., cocoa, coffee, green tea, black tea, herbal teas, lemonades, isotonic beverages, soft drinks, nectars, fruit and vegetable juices, and fruit or vegetable juice preparations), instant beverages (e.g., instant cocoa beverages, instant tea beverages, instant smoothies, instant milkshakes and instant coffee beverages), meat products (e.g., cold cuts, fresh or raw sausage preparations, seasoned oder, marinated fresh meat or salted meat products), eggs or egg products (e.g., dried whole egg, egg whites, and egg yolks), cereal products (e.g., breakfast cereals, muesli bars, and pre-cooked instant rice products), dairy products (e.g., whole fat or fat reduced or fat-free milk beverages, rice pudding, yoghurt, kefir, cream cheese, soft cheese, hard cheese, dried milk powder, ice cream, sherbet, whey, butter, buttermilk, and partly or wholly hydrolyzed products containing milk proteins), products produced from nuts (e.g., nut milks, nut butters, nut flours or powders), products from soy protein or other soy bean fractions (e.g., soy milk and products prepared thereof, beverages containing isolated or enzymatically treated soy protein, soy flour containing beverages, preparations containing soy lecithin, fermented products such as tofu or tempeh products prepared thereof and mixtures with fruit preparations and, optionally, flavoring substances), fruit preparations (e.g., jams, fruit ice cream, fruit sorbets, fruit smoothies, fruit sauces, and fruit fillings), vegetable preparations (e.g., ketchup, sauces, dried vegetables, deep-freeze vegetables, pre-cooked vegetables, and boiled vegetables), snack articles (e.g., chips, crisps, pretzels, biscuits, crackers and nuts), products on the basis of fat and oil or emulsions thereof (e.g., mayonnaise, remoulade, and dressings), other ready-made meals and soups (e.g., dry soups, instant soups, and pre-cooked soups), seasonings (e.g., sprinkle-on seasonings), sweetener compositions (e.g., tablets, sachets, and other preparations for sweetening beverages or other food). The present compositions may also serve as semi-finished products for the production of other compositions intended for nutrition or pleasure.

The composition of the present invention can also be present in the form of capsules, tablets (uncoated and coated tablets, e.g., gastro-resistant coatings), coated tablets, granules, pellets, solid-substance mixtures, dispersions in liquid phases, as emulsions, powders, solutions, pastes or other swallowable or chewable preparations, or as a dietary supplement.

For oral administration, tablets or capsules can be prepared by conventional means with acceptable excipients such as binding agents, fillers, lubricants, disintegrants, or wetting agents. The tablets can be coated, if desired. Preparations for oral administration also can be suitably formulated to give controlled release of the active ingredients. Liquid preparations for oral administration can take the form of, for example, solutions, syrups, or suspensions, or they can be presented as a dry product for constitution with saline or other suitable liquid vehicle before use.

The formulation described herein can also contain acceptable additives as will be understood by one skilled in the art, depending on the particular form of oral delivery. Non-limiting examples of such additives include suspending agents, emulsifying agents, non-aqueous vehicles, preservatives, buffer salts, flavoring, coloring, and sweetening agents as appropriate. Non-limiting examples of specific additives include: gelatin, glycerin, water, beeswax, lecithin, cocoa, caramel, titanium dioxide, and carmine.

In one embodiment, the adjuvant composition can be formulated for administration via injection, for example, as a solution or suspension. The solution or suspension can comprise suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid. One illustrative example of a carrier for intravenous use includes a mixture of 10% USP ethanol, 40% USP propylene glycol or polyethylene glycol 600 and the balance USP Water for Injection (WFI). Other illustrative carriers for intravenous use include 10% USP ethanol and USP WFI; 0.01-0.1% triethanolamine in USP WFI; or 0.01-0.2% dipalmitoyl diphosphatidylcholine in USP WFI; and 1-10% squalene or parenteral vegetable oil-in-water emulsion. Water or saline solutions and aqueous dextrose and glycerol solutions may be preferably employed as carriers, particularly for injectable solutions. Illustrative examples of carriers for subcutaneous or intramuscular use include phosphate buffered saline (PBS) solution, 5% dextrose in WFI and 0.01-0.1% triethanolamine in 5% dextrose or 0.9% sodium chloride in USP WFI, or a 1 to 2 or 1 to 4 mixture of 10% USP ethanol, 40% propylene glycol and the balance an acceptable isotonic solution such as 5% dextrose or 0.9% sodium chloride; or 0.01-0.2% dipalmitoyl diphosphatidylcholine in USP WFI and 1 to 10% squalene or parenteral vegetable oil-in-water emulsions.

Further components can be added to the compositions as are determined by the skilled artisan such as, for example, buffers, carriers, viscosity modifiers, preservatives, flavorings, dyes and other ingredients specific for an intended use. One skilled in this art will recognize that the above description is illustrative rather than exhaustive. Indeed, many additional formulations techniques and pharmaceutically-acceptable excipients and carrier solutions suitable for particular modes of administration are well-known to those skilled in the art In one embodiment, the supplement composition is formulated into a biosurfactant delivery system, wherein a biosurfactant forms a liposome, or micro- or nanocapsule, with the supplement composition encapsulated therein. In one embodiment, additional biological polymers can be included to provide further structure for encapsulation.

Biosurfactant encapsulation can enhance the bioavailability of the supplement composition by protecting it from components in the blood, such as proteins and other molecules, that otherwise might bind to the compound and prevent it from penetrating a target site. Additionally, the encapsulated delivery system can allow for compounds that might otherwise be degraded by acids or enzymes in the GI tract to be administered orally, as it creates a barrier against the acids or enzymes. Furthermore, the biosurfactant-encapsulated delivery system formulation allows for time release of the compound(s) therein, thereby reducing the potential toxicity or potential negative side-effects in a subject.

Methods for Improving the Quality of Life for Subjects with ASD

In certain embodiments, the present invention provides a method for improving the quality of life for a subject diagnosed with ASD or another condition, wherein the method comprises administering a therapeutically-effective amount of a supplement composition of the present invention to the subject.

Advantageously, the present invention can improve the quality of life for subjects who are diagnosed with, for example, ASD and/or a viral infection. "Improved quality of life" can include, for example, improvement of mental, emotional and/or physiological signs or symptoms of ASD, improvement in behavioral performance, and improvement in signs and symptoms of viral infections.

Signs and symptoms associated with ASD include, but are not limited to: irritability; hyperactivity; inattention; abnormalities in speech, verbal, communication, and language skills; repetitive behavior, including stereotypy, compulsive behavior, sameness (resistance to change), and ritualistic behavior; obsessive focus on certain topics and/or objects; inability to make eye contact; abnormalities in social interactions and/or understanding of others' feelings; anger issues and/or emotional outbursts; self-injury; and others.

Furthermore, the present invention can lead to treatment and/or prevention of other diseases, disorders, conditions, and/or comorbidities caused by and/or associated with ASD, including, but not limited to: anxiety, attention deficit disorder; brain inflammation; viral infections; clinical depression; Tourette syndrome; Fragile X syndrome; obsessive-compulsive disorder; bipolar disorder; learning disabilities; sensory disorders; developmental coordination disorder; disorders of the immune system and/or gastrointestinal system, including candidiasis; seizures and/or epilepsy; sleep disorders; increased risk of cancer; and others.

The subject of the present invention can be any human diagnosed with ASD, and/or with a condition wherein the immune system is activated and/or malfunctioning. In one embodiment, the subject is a child diagnosed with ASD or who exhibits the signs and symptoms thereof. In another embodiment, the subject has a compromised immune system, for example, due to genetics, illness, or because the subject previously contracted or was exposed to a viral or bacterial infection. The subject may presently be exhibiting signs of infection, or the subject may be asymptomatic because, for example, contraction of the virus occurred at some time in the past, e.g., in utero.

In specific embodiments, the subject has contracted or been exposed to a viral infection thought to be associated with alteration of immune system functioning and/or development of ASD, including but not limited to one or more of the following human herpes viruses (HHV): herpes simplex virus 1 (HSV-1), HSV-2, herpes zoster, varicella-zoster virus (VZV), cytomegalovirus (CMV), HHV6, HHV7, HHV8, Epstein-Barr virus (EBV) and Kaposi's sarcoma-associated herpesvirus (KSHV).

In some embodiments, the subject is infected with one or more HHVs and/or one or more additional viruses, such as, for example, rubella virus, measles virus, BK virus, JC virus, simian virus 40 (SR40), yellow fever, hepatitis, poliovirus, influenza, pneumovirus, paramyxovirus, coronavirus, HIV, leukemia virus, Simliki forest virus, HPV, Visna virus, vesicular stomatitits virus, respiratory syncytial virus, Dengue virus, or lymphocytic choriomeningitis.

In certain embodiments, the supplement composition can be used for enhancing the immune health of a subject infected with a viral agent, wherein the composition comprises ingredients that, for example, help support the immune system and suppress and/or disable infectious agents in the subject's body.

As used herein, "supporting" the immune system can include boosting, improving, enhancing, and/or maintaining the proper functioning of the immune system. Immune support can include support for the cells, tissues, and organs that contribute to proper functioning of the immune system, for example, the lymphatic system, spleen, bone marrow, or any other system involved in production of entities (e.g., antibodies, lymphocytes, red blood cells, white blood cells, platelets) that ward off foreign substances (e.g., pathogens such as viruses) from the body's normal and healthy tissues. Immune support can further include support for parts of the body that aid in preventing and healing from injury, inflammation, cancer, or other non-infectious diseases, ailments, or conditions.

In preferred embodiments, the methods comprise administering an amount of a supplement composition comprising tellimagrandin II, glycyrrhizin, monolaurin, selenium, one or more omega-3 fatty acids, honokiol, and a probiotic (e.g., *Bacillus coagulans* BC-30), wherein the amount is therapeutically-effective.

In one embodiment the supplement composition comprises, consists of, or consists essentially of tellimagrandin II, glycyrrhizin, monolaurin, selenium, omega-3 fatty acids, honokiol, and a probiotic (e.g., *Bacillus coagulans* BC-30). In certain embodiments, the supplement composition comprises, consists of, or consists essentially of therapeutically-effective amounts of each of these elements.

In certain embodiments, the supplement composition further comprises a biological amphiphilic molecule. In a specific embodiment, the biological amphiphilic molecule is a surfactant, preferably a biosurfactant. In one embodiment, the biological amphiphilic molecule is a saponin.

In one embodiment, the method first comprises testing the subject for, and/or diagnosing the subject with, ASD and/or another immune system-activating condition, such as a viral infection. In one embodiment, the method can first comprise testing the subject for signs of poor immune health, for example, by testing the subject for immune markers, such as T-cells and NK cells. In one embodiment, the testing is performed using known blood testing methods, including blood antibody tests, and in the case of viruses that cause, for example, external lesions, sampling, culturing and polynucleotide sequencing.

In one embodiment, the method further comprises performing follow-up tests on the subject to determine whether, and/or to what extent, the quality of life in a subject has improved. The subject can be monitored throughout the course of treatment, for example, every day or every other day, in order to determine the status of the infection and whether or not the method is effectively improving quality of life. This can include, for example, performing tests, such as those used for diagnosing ASD, as well as observing the subject for signs of improving health. If follow-up tests show that the rate of improved health is below that which is desired, the dosage of the composition can be adjusted as determined by the skilled practitioner.

In preferred embodiments of the present invention, administration of the supplement composition occurs daily for several days or weeks. Administration can include any known method of drug administration, including, but not limited to, oral, nasal, cutaneous (e.g., applying it as a cream), or intravenous administration.

In one embodiment, the supplement composition is administered to the subject once, twice, or three times per day, determined on a subject-by-subject basis by a skilled physician. Factors to be considered when determining the number of doses to administer include the age of the individual receiving treatment, whether the subject is or may be pregnant (if the subject is female) and the severity of the subject's symptoms.

The methods of the present invention can be utilized alongside traditional antiviral treatments as a supplement thereto. For example, in some embodiments, the methods can further comprise administering an antiviral drug. The antiviral can be, for example, alacyclovir, acyclovir, famciclovir, ganciclovir, valganciclovir, ribavirin, brivudin, cidofovir, fomivirsen, foscarnet, penciclovir, vidarabine and others used to treat chronic, congenital, persistent, latent, dormant, acute and/or subacute viral infections.

In some embodiments, the methods disclosed herein can also include measuring a baseline of behavioral performance and/or overall health prior to treatment of the subject according to the subject methods, and/or measuring the behavioral performance and/or overall health after treatment. The methods can include comparing the behavioral performance and/or overall health prior to and after treatment is administered to the subject, and the comparison can be used to determine if and to what extent the behavioral performance and/or overall health in the subject is improved, or if adjustments should be made to the treatment given.

As used herein, the phrase "improvement in behavioral performance" refers to reduction in the severity or frequency, to whatever extent, of one or more of the behavioral disorders, symptoms and/or abnormalities expressed by an individual suffering from ASD, or a pathological condition having behavioral symptoms similar to those of ASD. The improvement is either observed by the individual taking the treatment themselves or by another person (medical professional or otherwise).

In the method disclosed herein, behavioral performance can be measured and evaluated using various parameters and methods. For example, behavioral tests can be conducted to determine the presence and/or extent of restricted repetitive behavior and/or stereotyped behavior patterns of the subject under test. In some embodiments, the Autism Behavior Checklist (ABC), Autism diagnostic Interview-Revised (ADI-R), childhood autism Rating Scale (CARS), and/or Pre-Linguistic Autism Diagnostic Observation Schedule (PL-ADOS) is used for the behavioral test. The behavioral test can include, but is not limited to, detecting the presence and/or extent of (1) preoccupation with one or more stereotyped and restricted patterns of interest that is abnormal in either intensity or focus; (2) inflexible adherence to specific, nonfunctional routines or rituals; (3) stereotyped and repetitive motor mannerisms (such as hand flapping, finger flapping etc.); and/or (4) persistent preoccupation with parts of objects. Non-limiting examples of behavior that can be included in a behavioral test and suggest a need for improving behavioral performance in the subject under the test include:

(a) Sensory behaviors: poor use of visual discrimination when learning; seems not to hear, so that a hearing loss is suspected; sometimes shows no "startle response" to loud noise; sometimes painful stimuli such as bruises, cuts, and injections evoke no reaction; often will not blink when bright light is directed toward eyes; covers ears at many sounds, squints, frowns, or covers eyes when in the presence of natural light; frequently has no visual reaction to a "new" person; stares into space for long periods of time;

(b) Relating behaviors: frequently does not attend to social/environmental stimuli; has no social smile; does not reach out when reached for; non-responsive to others' facial expressions/feelings; actively avoids eye contact; resists being touched or held; is flaccid when held in arms; is stiff and hard to hold; does not imitate other children at play; has not developed any friendships; is often frightened or very anxious; "looks through" people;

(c) Body and object use behaviors: whirls self for long periods of time; does not use toys appropriately; insists on keeping certain objects with him/her; rocks self for long periods of time; frequently lunges and darts; flaps hands; walks on toes; hurts self by banging head, biting hand, etc.; twirls, spins, and bangs objects frequently; will feel, smell, and/or taste objects in the environment; performs complicated "rituals" such as lining things up; is very destructive; and (d) Language behaviors: does not follow simple commands given once; has pronoun reversal; speech is atonal; does not respond to own name when called out among others; seldom says "yes" or "I"; does not follow simple commands involving prepositions; uses gestures to get desired objects; repeats phrases over and over; cannot point to more than five named objects; uses 0-5 spontaneous words per day to communicate wants and needs; repeats sounds or words over and over; echoes questions or statements made by others; uses at least 15 but less than 30 spontaneous phrases daily to communicate; learns a simple task but "forgets" quickly; has strong reactions to changes in routine/environment; has "special abilities" in one area of development, which seems to rule out mental retardation; has severe temper tantrums and/or frequent minor tantrums; hurts others by biting, hitting, kicking, etc.; does not wait for needs to be met; has difficulties with toileting; does not dress self without frequent help; is frequently unaware of surroundings and may be oblivious to dangerous situations; prefers to manipulate and be occupied with inanimate things; and a developmental delay was identified at or before 30 months of age.

One of ordinary skill in the art would appreciate that the attending physician would know how to identify a subject in need of treatment disclosed herein.

REFERENCES

Abdallah, H. M., Al-Abd, A. M., El-Dine, R. S., & El-Halawany, A. M. (2015). P-glycoprotein inhibitors of natural origin as potential tumor chemo-sensitizers: A review. Journal of Advanced Research, 6(1), 45-62. doi: 10.1016/j.jare.2014.11.008

Baba M, Shigeta S. (1987). Antiviral activity of glycyrrhizin against varicella-zoster virus in vitro. Antiviral Res 7:99-107.

Beck, M. (2001). Selenium as an antiviral agent. *Selenium,* 235-245. doi: 10.1007/978-1-4615-1609-5_19.

Borsanyiova, M., Patil, A., Mukherji, R., Prabhune, A., & Bopegamage, S. (2015). Biological activity of sophorolipids and their possible use as antiviral agents. Folia Microbiologica, 61(1), 85-89. doi:10.1007/s12223-015-0413-z Garima Bhardwaj, Swaranjit Singh Cameotra and Harish Kumar Chopra. (2013). Biosurfactants from Fungi: A Review. Pet Environ Biotechnol, 4:6 DOI: 10.4172/2157-7463.1000160

Kesarwani, K., & Gupta, R. (2013). Bioavailability enhancers of herbal origin: An overview. Asian Pacific Journal of Tropical Biomedicine, 3(4), 253-266. doi:10.1016/s2221-1691(13)60060-x Lalita, Badam. (1994). In vitro studies on the effect of glycyrrhizin from Indian *Glycyrrhiza glabra* Linn on some RNA and DNA viruses. Indian Journal of Pharmacology. The J. of Pharm. and Exper. Ther. Vol. 297, No. 1.

Lieberman, S., Enig, M. G., & Preuss, H. G. (2006). A Review of Monolaurin and Lauric Acid: Natural Virucidal and Bactericidal Agents. Alternative and Complementary Therapies, 12(6), 310-314. doi:10.1089/act.2006.12.310

Lin, J.-C., Cherng, J.-M., Hung, M.-S., Baltina, L. A., Baltina, L., & Kondratenko, R. (2008). Inhibitory effects of some derivatives of glycyrrhizic acid against Epstein-Barr virus infection: Structure-activity relationships. Antiviral Research, 79(1), 6-11. doi:10.1016/j.antiviral.2008.01.160

Marcos Roberto de Oliveira, Agnes Magri, Cristiani Baldo, Doumit Camilios-Neto, Tamires Minucelli, Maria Antonia Pedrine Colabone Celligoi. (2015). Review: Sophorolipids A Promising Biosurfactant and it's Applications. International Journal of Advanced Biotechnology and Research(IJBR) ISSN 0976-2612, Online ISSN 2278-599X, Vol 6, Issue 2, 2015, pp 161-174

Masahiko Kurokawa, Toyoharu Hozumi, Minako Tsurita, Shigetoshi Kadota, Shigetoshi Kadota, Tsuneo Namba, and Kimiyasu Shiraki. (2001). Biological Characterization of Eugeniin as an Anti-Herpes Simplex Virus Type 1 Compound in Vitro and in Vivo. J Pharmacol Exp Ther. 2001 April; 297(1):372-9.

Masahiko Kurokawa, Tomomi Shimizu, Wataru Watanabe and Kimiyasu Shiraki. (2010). Development of New Antiviral Agents from Natural Products. The Open Antimicrobial Agents Journal, 2010, 2, 49-57

Numazaki, K. Umetsu, M., Chiba, S. (1994). Effect of Glycyrrhizin in Children with Liver Dysfunction Associated with Cytomegalovirus Infection. Tohoku J. Exp. Med., 172 (2), 147-153.

Rayman, M. P. (2012). Selenium and human health. The Lancet, 379(9822), 1256-1268. doi:10.1016/s0140-6736(11)61452-9

Rodrigues, L., Banat, I. M., Teixeira, J., & Oliveira, R. (2006). Biosurfactants: potential applications in medicine. Journal of Antimicrobial Chemotherapy, 57(4), 609-618. doi:10.1093/jac/dk1024

Schreier, S., Malheiros, S. V. P., & de Paula, E. (2000). Surface active drugs: self-association and interaction with membranes and surfactants. Physicochemical and biological aspects. Biochimica et Biophysica Acta (BBA)-Biomembranes, 1508(1-2), 210-234. doi:10.1016/s0304-4157 (00) 00012-5

Sun, Y., Song, M., Niu, L., Bai, X., Sun, N., Zhao, X., . . . Li, H. (2013). Antiviral effects of the constituents derived from Chinese herb medicines on infectious bursal disease virus. Pharmaceutical Biology, 51(9), 1137-1143. doi: 10.3109/13880209.2013.781197

Yukawa, T. A., Kurokawa, M., Sato, H., Yoshida, Y., Kageyama, S., Hasegawa, T., Shiraki, K. (1996). Prophylactic treatment of cytomegalovirus infection with traditional herbs. Antiviral Research, 32(2), 63-70. doi: 10.1016/0166-3542(95)00978-7

Xiao-Hong Cao, Zhen-Yu Liao, Chun-Ling Wang, Wen-Yan Yang, and Mei-Fang Lu. (2009). Evaluation of a lipopeptide biosurfactant from *Bacillus* natto TK-1 as a potential source of anti-adhesive, antimicrobial and antitumor activities. Braz J Microbiol. 2009 April-June; 40(2): 373-379. Published online 2009 Jun. 1. doi: [10.1590/S1517-838220090002000030]

We claim:

1. A method for improving the quality of life in a subject diagnosed with autism spectrum disorder (ASD), wherein the method comprises, in the following order:

a) conducting blood test on the subject's blood wherein one blood test assesses immune system health of the subject and another blood test determines the presence or absence of a viral infection in the subject;

b) administering to the subject an antiviral drug selected from valacyclovir, acyclovir, famciclovir, ganciclovir, valganciclovir, ribavirin, brivudin, cidofovir, fomivirsen, foscarnet, penciclovir, and vidarabine;

c) administering to the subject alpha-lipoic acid, honokiol and monolaurin; and d) performing a follow-up test on the subject to determine to what extent, the subject's quality of life is improved as a result of the administration of the antiviral drug, alpha-lipoic acid, honokiol and monolaurin;

wherein the follow-up test establishes that the method improves the quality of life of the subject by improving, in the subject, at least one sign or symptom associated with ASD, wherein the sign or symptom is selected from abnormalities in speech, verbal, communication, and/or language skills; repetitive behavior; stereotypy; sameness (resistance to change); ritualistic behavior; obsessive focus on certain topics and/or objects; and inability to make eye contact.

2. The method according to claim 1, wherein the follow-up test establishes that the subject has decreased repetitive behavior.

3. The method according to claim 1, wherein the follow-up test establishes that the subject has increased eye contact.

* * * * *